United States Patent [19]

Schirmann et al.

[11] Patent Number: 5,154,912
[45] Date of Patent: Oct. 13, 1992

[54] $O^{17}$ ISOTOPIC PEROXIDES

[75] Inventors: Jean-Pierre Schirmann, Ouillins; Jean-Jacques Barieux, Villeurbanne, both of France

[73] Assignee: Atochem, Puteaux, France

[21] Appl. No.: 587,176

[22] Filed: Sep. 20, 1990

Related U.S. Application Data

[63] Continuation of Ser. No. 411,904, Aug. 14, 1989, abandoned, which is a continuation of Ser. No. 152,028, Feb. 3, 1988, abandoned.

[30] Foreign Application Priority Data

Feb. 3, 1987 [FR] France .................. 87 01282

[51] Int. Cl.$^5$ .............. C01B 15/01; C01B 15/023; C07C 409/00
[52] U.S. Cl. .................. 423/584; 423/588; 423/582; 556/9; 556/12; 556/27; 556/28; 556/30; 556/31; 556/69; 556/70; 556/76; 556/77; 556/85; 556/87; 556/94; 556/172; 556/173; 556/174; 556/178; 556/179; 556/181; 556/183; 556/419; 556/428; 556/437; 556/443; 556/449; 560/302; 560/303; 560/318; 562/1; 562/2; 562/30; 564/164; 564/182; 564/191; 564/197; 568/558; 568/564; 568/568; 568/571

[58] Field of Search ............ 423/588, 584, 582; 556/9, 12, 27, 28, 30, 31, 69, 70, 76, 77, 85, 87, 94, 172, 173, 174, 178, 179, 181, 183, 419, 428, 437, 443, 449; 560/302, 303, 318; 562/1, 2, 30; 564/182, 164, 191, 197; 568/564, 568, 571, 558

[56] References Cited

U.S. PATENT DOCUMENTS 3,755,552  8/1973  Lee et al. ................. 423/588

OTHER PUBLICATIONS

Chemical Abstracts 103:170875b.
Baumstark et al., (Tetrahedron Letters, vol. 26, No. 17, pp. 2051-2054 (1985)).
Curci et al., (Journal of Molecular Catalysis, 32 (1985) 251-257).
Helvetica Chimica Acta, vol. XLIV, Nos. 98-99, pp. 865-880.
European Search Report.

*Primary Examiner*—Wayne Langel
*Attorney, Agent, or Firm*—Burns, Doane, Swecker & Mathis

[57] ABSTRACT

The peroxides which include the $O^{17}$ isotope, especially the hydrogen peroxides and peroxides and hydroperoxides prepared therefrom, are well adapted as nonradioactive labeled compounds for use in the medicinal and biological arts.

9 Claims, No Drawings

$O^{17}$ ISOTOPIC PEROXIDES

This application is a continuation of application Ser. No. 07/411,904, filed Aug. 14, 1989, abandoned, which is a continuation of Ser. No. 07/152,028 filed Feb. 3, 1988, abandoned.

BACKGROUND OF THE INVENTION

Field of the Invention

The present invention relates to novel isotopic ($O^{17}$) peroxide compounds, to a process for the preparation of such $O^{17}$ isotopes, and to the use of these compounds as labeled molecules and as intermediates in the synthesis of other labeled molecules.

SUMMARY OF THE INVENTION

The peroxide compounds according to this invention are characterized in that either or both of the oxygen atoms constituting the —O—O— peroxide group are $O^{17}$ isotopes, whether in whole or in part.

Among these compounds, the invention especially relates to compounds wherein more than 0.1% by weight of the peroxide oxygen —O—O— comprises the $O^{17}$ isotope, this proportion preferably being greater than 1% and less than 80%. As the $O^{17}$ isotope is associated with $O^{16}$, such peroxide group which is characteristic of the compounds according to the invention shall for the sake of simplicity be represented as —$O^{16}$—$O^{17}$—, with the understanding that this representation is not intended to limit the invention to a $O^{16}/O^{17}$ distribution in equal parts, as the characterization given above concerning the number of $O^{17}$ isotopes in the —O—O— peroxide group remains valid.

DETAILED DESCRIPTION OF THE PREFERRED EMBODIMENTS OF THE INVENTION

More particularly according to the present invention, the subject isotopic peroxide compounds advantageously have the formulae:

R—$O^{16}$—$O^{17}$—R'tm (I)

or

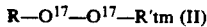

R—$O^{17}$—$O^{17}$—R'tm (II)

wherein R and R', which may be identical or different, are each a hydrogen atom; an $R_1$ linear or branched chain alkyl, alkenyl, alkynyl, cycloalkyl, alkoxy or cycloalkoxy, or aryl radical, or an inorganic, organometallic or organometalloidal group, the latter containing at least one of said $R_1$ radicals and a metal or metalloid selected from among Al, Ge, Pb, P, Li, Sn, Sb, Te, Se, As, B, with the proviso that such organometal or metalloid group may itself comprise one or more —$O^{16}$—$O^{17}$ groups; or one of the radicals:

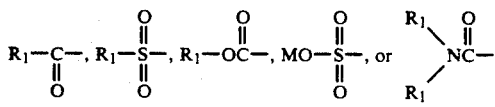

in which $R_1$ is as above defined and M is a hydrogen atom or an alkali metal, said radicals $R_1$ containing up to 20 carbon atoms and optionally being substituted by one or more fluorine, chlorine or bromine atoms or —OH or —$NO_2$ groups, with the further proviso that R and R' may together form a divalent atom or group T, such divalent group T itself comprising a wholly hydrocarbon radical or one or more —$O^{16}$—$O^{17}$— linkages, the free valences of which optionally being bonded to organic or inorganic moieties.

Exemplary of such divalent atoms or groups T, the following are particularly representative: atoms of calcium, magnesium, barium, zinc, cadmium, and the groups —CH($CH_3$)—O—CH($CH_3$)—, —$CH_2$—O—$CH_2$—, $B(OH)_2$—$O^{16}$—$O^{17}$—$B(OH)_2$—, —C($CH_3$)$_2$—$O^{16}$—$O^{17}$—C($CH_3$)$_2$—, —C($CH_3$)($C_2H_5$)—$O^{16}$—$O^{17}$— C($CH_3$)($C_2H_5$)—,

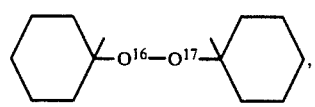

—C($CH_3$)$_2$—$O^{16}$—$O^{17}$—C($CH_3$)$_2$—$O^{16}$—$O^{17}$—C($CH_3$)$_2$—.

Accordingly, this invention features hydrogen peroxide containing the $O^{17}$ isotope, as well as the hydroperoxides, peroxides, peracids, peresters and more generally the entirety of the peroxide compounds and, in particular, those peroxide compounds that may be prepared from hydrogen peroxide.

Preferred are those compounds of Formula (I) or (II) wherein at least one of the symbols R and R' (the other may represent hydrogen) is a methyl, ethyl, isopropyl, n-butyl, t-butyl, t-amyl, cyclohexyl, methoxy, ethynyl, propyn-2-yl, p-diisopropylphenyl, 1-methylcyclohexyl, 1,2,3,4-tetrahydronaphth-1-yl, acetyl, propionyl, isobutyryl, pivaloyl, stearoyl, acryloyl, oleoyl, benzyloyl, nonanoyl, palmitoyl, chloroacetyl, trichloroacetyl, trifluoroacetyl or 4-chlorobenzoyl radical.

Exemplary of the peroxide compounds according to the invention which include —$O^{17}$— in the peroxide group, the following are representative:

(i) methyl, ethyl, isopropyl, n-, sec- and t-butyl, t-anyl, cyclohexyl, 1,1,3,3-tetramethyl, butyl, 1-methoxycyclohexyl, and stearyl hydroperoxides;

(ii) hydroxyhydroperoxides of the formula $R_3CH(OOH)(OH)$, wherein $R_3$ is H, $CH_3$, $CCl_3$, n—$C_4H_9$, n—$C_7H_{15}$ or n—$C_8H_{17}$;

(iii) hydroperoxides of the formula $[R_4H(OH)CO]_2$, wherein $R_4$ is H, $CH_3$, $CCl_3$, n—$C_4H_9$, n—$C_7H_{15}$ or n—$C_8H_{17}$;

(iv) 2-chloro-1-hydroperoxycyclohexanol;

(v) 1,1-dioxy-bis-cyclohexanol;

(vi) 3,3,6,6-tetramethyl-1,2,4,5-tetroxane;

(vii) 3,3,6,6,9,9-hexamethyl-1,2,4,5,7,8-hexoxanane;

(vii) 1,2,4-trioxolane;

(iv) 3,5-dimethyl-1,2,4-trioxalane;

(v) 3,5-diphenyl-1,2,4-trioxalane;

(vi) dimethyl, perfluorodimethyl, diethyl, t-butylmethyl, diisopropyl, perfluoro-di-t-butyl and dicumyl peroxides;

(vii) sodium peroxyborate tetrahydrate or monohyrate;

(viii) dioxybis(triethyltin);

(xiv) performic, peracetic, peroxypropionic, peroxybutyric, perbenzoic, m-chloroperbenzoic, diperoxyphthalic, diperoxyhexanoic, trifluoroperacetic and trichloroperacetic acids;

(xv) diacetyl, bis(chloroacetyl), acetylbenzoyl, dioctanoyl, bis(phenylacetyl), bis(trichloroacetyl) and bis(trifluoroacetyl)peroxides;

(xvi) ethyl, diisopropyl and dicyclohexyl peroxydicarbonates;

(xvii) bis(methylsulfonyl), acetyl-t-butylsulfonyl, acetylcyclohexylsulfonyl, bis(benzenesulfonyl) and bis(benzenesulfonyl)peroxides;

(xviii) t-cumylperacetate, t-butylperbenzoate and di-t-butyldiperoxyadipate; and (xix) diisopropylperoxydicarbonate and t-butylperoxypivalate.

The present invention also features a process for the preparation of the aforedescribed peroxide compounds, wherein the oxygen content is entirely or partially comprised of the $O^{17}$ isotope. In other words, either $O^{17}$ along, or $O^{16}$ enriched in $O^{17}$ characterizes the peroxides of the invention.

The $O^{17}$ isotope exists in nature in very low concentrations (0.04%) and the isolation, per se, of this $O^{17}$ isotope, or the enrichment of $O^{16}$ with $O^{17}$, are not in and of themselves within the ambit of this invention. Such techniques, which include, for example the fractional distillation of electrolysis of heavy water, or separation by laser, are described in the literature.

The first peroxide compound according to the invention (hydrogen peroxide) may be prepared very advantageously via the oxidation/reduction of quinones. According to this process, the quinone and more precisely anthraquinone or alkylanthraquinones are hydrogenated, generally in the presence of a catalyst, such as Raney nickel or palladium on activated alumina, and then oxidized.

In the process according to the invention, either $O^{17}$ oxygen or $O^{16}$ oxygen enriched in $O^{17}$ is substituted for air, or air enriched in $O^{17}$ oxygen is used. The hydrogenation reaction is typically carried out in the solvent phase, such solvents comprising, for example, acetic, propionic, adipic, succinic, or sebacic acid esters, optionally mixed with alcohols, in mixtures of alcohols and dicarboxylic acids, and in mixtures of alcohols and substituted naphthalene.

The solution resulting from the hydrogenation is oxidized, as indicated above, and then washed to extract an aqueous solution of $H-O^{16}-O^{17}-H$ and/or $H_2O_2^{17}$ hydrogen peroxide.

The hydrogen peroxide according to the invention has all of the physical and chemical properties of $O^{16}$ hydrogen peroxide. It further has magnetic resonance spectrum characterized by a chemical displacement of $\delta = 180$ ppm relative to $H_2O^{17}$ used as the reference. Its mass spectrum clearly indicates the presence of the m/e ion of the related peaks of 36 and 35.

Advanced nuclear magnetic resonance instruments make it possible to identify the $O^{17}$ oxygen atom and to determine the proportion of enrichment.

The other peroxide compounds according to the present invention may generally be prepared by known methods, with the $O^{17}$ isotope being employed at any time during the preparation of such peroxide compounds.

However, a particularly preferred method comprises preparing the peroxide compounds from the hydrogen peroxide $H_2O_2^{17}$ or $H-O^{16}-O^{17}-H$ described above, either along or combined with $H_2O_2^{16}$.

The alkyl hydroperoxides may be prepared from alkyl halides or tertiary alcohols by reaction with $H_2O_2^{17}$ or $H-O^{16}-O^{17}-H$ in an acid medium. It is also possible to prepare them by the direct oxidation of the corresponding hydrocarbons with $O_2^{17}$ or $-O^{17}-O^{16}$.

The hydroxy or dihydroxyhydroperoxides or peroxides may be prepared from $H_2O_2^{17}$ or $H-O^{16}O^{17}-H$ and aldehydes or ketones.

Dialkyl peroxides may be prepared from $H_2O_2^{17}$ or $H-O^{16}-O^{17}-H$ and an appropriate reagent, which, depending on the conditions of the reactions and specifically the acidity or basicity of the reaction medium may comprise dialkyl sulfate, dialkyl sulfonate, alkyl halides, alcohols, glycols, ethers, esters, amines, amides or compounds containing an olefinic double done, such as acyclic and cyclic olefin hydrocarbons, vinyl and isopropenyl ethers, enamines, N-vinylamides, vinylsulfonates, divinyl sulfones, $\alpha,\beta$-unsaturated compounds, such as methyl acrylate, acrylamide, acrylonitrile, and the like.

Peracids may be produced by the equilibrium reaction of hydrogen peroxide with a carboxylic acid, under acid catalysis.

The diacyl peroxides may be prepared by the reaction, in the presence of a base, of an acyl chloride or an acid anhydride with hydrogen peroxide, sodium peroxide or a peracid.

The peresters may be prepared by the reaction of an alkyl hydroperoxide with an acylation agent, such as an acyl chloride, anhydride, ketene, a sulfonyl chloride, phosgene, an alkyl chloroformate, isocyanate, carbamoyl chloride, or carboxylic acid or ester thereof.

The immediately above features preparing the different peroxide compounds according to the invention from hydrogen peroxide. Obviously, however, the invention is not limited to such process and any mode of preparation of the compounds of, e.g., Formula I is intended, which peroxide compounds include the $O^{17}$ isotope.

The peroxide compounds according to the invention themselves constitute labeled molecules due to the presence of the $O^{17}$ isotope. Consequently, they may be used for the study of numerous reactions and, in particular, oxidation reactions comprising the transfer of the oxygen atom to the reducing agent, whether in vivo or in vitro.

These compounds may also, in view of their peroxide nature, be used in the preparation of a large number of other labeled molecules. Among such molecules, which are also within the scope of this invention, the following are particularly representative, and are prepared from hydroperoxides or peroxides:

(1) Alcohols produced by the reduction of alkyl hydroperoxides;

(2) Unsaturated acids and esters, from aldehydes and peroxide compounds;

(3) Hydroxylamines, imines and nitrones from amines and peroxide compounds;

(4) Carboxylic acids, from ketones and peroxide compounds;

(5) Phosphine oxides, from phosphines and peroxide compounds;

(6) Sulfoxides, from sulfides and peroxide compounds;

(7) Alcohols and phenols, from Grignard reagents and peroxide compounds;

(8) Epoxides, from olefins and peroxide compounds;

(9) Phenols, from aromatic compounds and peroxide compounds;

(10) Amides, from nitriles;

(11) Ketones, from secondary alcohols and peroxide compounds;

(12) Quinones, form phenols and peroxide compounds.

From the foregoing categories of products, especially representative are: methanol, ethanol, propanol, isopropanol, benzyl alcohol, acetone, methylethylketone, cyclohexanone, mesityl oxide, diacetone alcohol, acetophenone, benzophenone, formol, acetaldehyde, propionaldehyde, the butyraldehydes, acrolein, crotonaldehyde, formic acid, acetic acid, propionic acid, the butyric acids, amino acids, acrylic acid, methacrylic acid, benzoic acid, para-nitrobenzoic acid, glutaric acid, oxalic acid, succinic acid, adipic acid, the phthalic acids, acetic anhydride, maleic anhydride, phthalic anhydride, phenol, pyrocatechol, hydroquinone, naphthoquinone, anthraquinone, 2-ethylanthraquinone, methyl acetate, ethyl acetate, butyrolactone, caprolactone, formamide, acetamide, benzamide, and the like.

The subject labeled molecules are suitable for a large number of applications, in particular in the fields of medicine and biology, where the presence of the $O^{17}$ isotope makes it possible, in view of its non-radioactivity, to determine metabolic pathways.

In order to further illustrate the present invention and the advantages thereof, the following specific examples are given, it being understood that same are intended only as illustrative and in nowise limitative.

EXAMPLE 1

In the presence of a catalyst consisting of 2% palladium deposited onto a silicoaluminate carrier, a prepared solution was hydrogenated which contained 66.8 g/liter of 5,6,7,8-tetrahydro-2-ethylanthraquinone and 6.7 g/liter 2-ethylanthraquinone, or 73.5 g/liter of total solute, in a solvent consisting of 57% by volume of methylcyclohexyl acetate and 43% by volume of a $C_9$ aromatic hydrocarbon fraction. The hydrogenation was carried out at 70° C. After is was completed, the gaseous phase was carefully purged from the reactor with nitrogen. The hydrogenated phase, maintained under nitrogen, was separated from the catalyst and an aliquot fraction of 200 g of solution was introduced into a 500 ml reactor and heated to 70° C. Under pressure, 0.9 liter of enriched oxygen ($O^{17}=10\%$) was then progressively introduced. When the absorption of oxygen ceased, the resulting reaction mixture was twice subjected to extraction with 400 ml of distilled water, successively. The two aqueous extracts were combined and by iodometry 0.03 mole hydrogen peroxide was determined, which corresponded to a yield of 80%.

$O^{17}$ NMR analysis provided a spectrum which showed a resonance peak having a chemical displacement of $\delta=180$ ppm in water, with (commercial) $H_2O^{17}$ serving as the internal reference. The identification was confirmed by mass spectrometry, which gave two related peaks with respective masses of 35 and 36 corresponding to $H-O^{17}-O^{17}-H$ and $H-O^{16}-O^{17}-H$.

EXAMPLE 2

Into a 500 ml reactor containing 300 ml anhydrous ether, equipped with agitation means and cooled to $-70°$ C., 0.9 liter of enriched oxygen ($O^{17}\approx 10\%$) and 70 ml of an ether (0.53 molar %) solution of tert-butyl magnesium were simultaneously and slowly added over the course of 75 minutes. The temperature was permitted to slowly rise to 0° C., whereupon a slow hydrolysis was effected by the dropwise addition of 50 ml dilute hydrochloric acid (0.72 N). After decantation and the extraction of the aqueous phase with 100 ml ether, the ether phase was collected and its volume adjusted to 500 ml. Iodometric analysis evidenced that 2.72 g tert-butyl hydroperoxide had been formed, corresponding to a yield of 86% relative to magnesium and 80% relative to the oxygen introduced. $O^{17}$ NMR analysis provided the following results, using $H_2O^{17}$ as the internal reference:

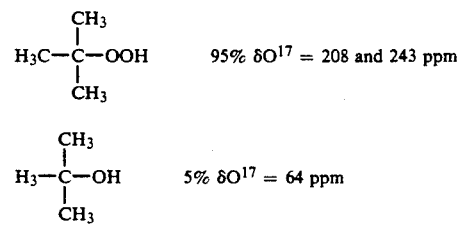

EXAMPLES 3 TO 5

To 2 cm³ of an aqueous solution of hydrogen peroxide labeled with $O^{17}$ and prepared according to the procedure of Example 1, the following carboxylic acid component was added, at room temperature: acetic, propionic, trifluoroacetic acid, together with a trace of sulfuric acid. The reaction was carried out for 2 hr and the reaction mixture was examined by $O^{17}$ NMR analysis. The formation of the corresponding labeled percarboxylic acids was determined. The corresponding labeled carboxylic acids may be produced in the same manner with $H_2O^{17}$. The chemical displacements were the following, using $H_2O^{17}$ as the internal reference:

| | $R-C-O^{17}-H$ (*) | $R-C-O-O^{17}-H$ (**) |
|---|---|---|
| | $\parallel$ | $\parallel$ |
| | O | O |
| $CH_3-COOH$ | $\delta = 255$ | $\delta = 273$ |
| $C_2H_5-COOH$ | $\delta = 254$ | $\delta = 266$ and 280 |
| $CF_3-COOH$ | $\delta = 245$ | $\delta = 260$ and 280 |

(* the 2 Os are equivalent and gave a single band)
(** the yields corresponded to the peroxide oxygens;

the $\diagdown$C=O was determined around $\delta$ 332)

EXAMPLE 6

10 cm³ of an ether solution produced as in Example 1 were reacted with 10 cm³ of 10% sulfuric acid. By $O^{17}$ NMR, the formation of di-tert-butyl peroxide $\delta O^{17}=269$ ppm (internal reference $H_2O^{17}$) was determined.

EXAMPLE 7

To 2 cm³ of an aqueous solution of hydrogen peroxide labeled with oxygen-17 and prepared as in Example 1, 10 cm³ 10% sulfuric acid and 2 cm³ tert-butanol were added at room temperature. By $O^{17}$ NMR, the formation of di-tert-butyl peroxide, characterized by a chemical displacement $\delta O^{17}=269$ ppm (internal reference $H_2O^{17}$), was determined.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An isotopic peroxide comprising more than 0.1% by weight of $O^{17}$ oxygen in the —O—O— group thereof having one of the general formulae:

$$R-O^{16}-O^{17}-R' \qquad (I)$$

or $$R-O^{17}-O^{17}-R' \qquad (II)$$

wherein R and R', which may be identical or different, are each a hydrogen atom; an $R_1$ linear or branched chain alkyl, alkenyl, alkynyl, cycloalkyl, alkoxy or cycloalkoxy, or aryl radical, or an inorganic, organometallic or organometalloidal group, the latter containing at least one of said $R_1$ radicals and a metal or metalloid comprising Al, Ge, Pb, P, Li, Sn, Sb, Te, Se, As or B, with the proviso that such organometal or metalloid group may itself comprise one or more —$O^{16}$—$O^{17}$ groups; or one of the radicals:

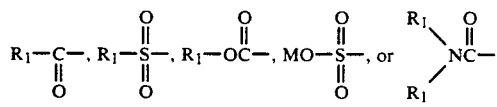

in which $R_1$ is as above defined and M is a hydrogen atom or an alkali metal, said radicals $R_1$ containing up to 20 carbon atoms and optionally being substituted by one or more fluorine, chlorine or bromine atoms or —OH or —$NO_2$ groups, with the further proviso that R and R' may together form a divalent atom or group T, such divalent group T itself comprising a wholly hydrocarbon radical or one or more —$O^{16}$—$O^{17}$— linkages, the free valences of which being bonded to organic or inorganic moieties.

2. The isotopic peroxide as defined by claim 1, comprising a hydrogen peroxide, a hydroperoxide, a peroxide, a peracid, or a perester.

3. The isotopic peroxide as defined by claim 1, wherein at least one of the symbols R and R' is a methyl, ethyl, isopropyl, n-butyl, t-butyl, t-amyl, cyclohexyl, methoxy, ethynyl, propyn-2-yl, p-diisopropylphenyl, 1-methylcyclohexyl, 1,2,3,4-tetrahydronaphth-1-yl, acetyl, propionyl, isobutyryl, pivaloyl, stearoyl, acryloyl, oleoyl, benzyloyl, nonanoyl, palmitoyl, chloroacetyl, trichloroacetyl, trifluoroacetyl or 4-chlorobenzoyl radical.

4. The isotopic peroxide as defined by claim 3, wherein either R or R' is a hydrogen atom.

5. A composition comprising isotopic peroxides comprising more than 0.1% by weight of $O^{17}$ oxygen in the —O—O— group thereof having the general formula:

$$R-O^{16}-O^{17}-R' \qquad (I)$$

and the general formula:

$$R-O^{17}-O^{17}-R' \qquad (II)$$

wherein R and R' in both formula (I) and formula (II), which may be identical or different, are each a hydrogen atom; an $R_1$ linear or branched chain alkyl, alkenyl, alkynyl, cycloalkyl, alkoxy or cycloalkoxy, or aryl radical, or an inorganic, organometallic or organometalloidal group, the latter containing at least one of said $R_1$ radicals and a metal or metalloid comprising Al, Ge, Pb, P, Li, Sn, Sb, Te, Se, As or B, with the proviso that such organometal or metalloid group may itself comprise one or more —$O^{16}$—$O^{17}$ groups; or one of the radicals:

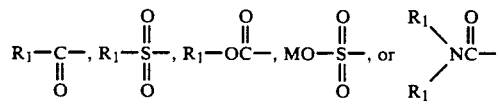

in which $R_1$ is as above defined and M is a hydrogen atom or an alkali metal, said radicals $R_1$ containing up to 20 carbon atoms and optionally being substituted by one or more fluorine, chlorine or bromine atoms or —OH or —$NO_2$ groups, with the further proviso that R and R' may together form a divalent atom or group T, such divalent group T itself comprising a wholly hydrocarbon radical or one or more —$O^{16}$—$O^{17}$— linkages, the free valences of which being bonded to organic or inorganic moieties.

6. The isotopic peroxide as defined by claim 5, comprising a hydrogen peroxide, a hydroperoxide, a peroxide, a peracid, or a perester.

7. The isotopic peroxide as defined by claim 5, wherein at least one of the symbols R and R' is a methyl, ethyl, isopropyl, n-butyl, t-butyl, t-amyl, cyclohexyl, methoxy, ethynyl, propyn-2-yl, p-diisopropylphenyl, 1-methylcyclohexyl, 1,2,3,4-tetrahydronaphth-1-yl, acetyl, propionyl, isobutyryl, pivaloyl, stearoyl, acryloyl, oleoyl, benzyloyl, nonanoyl, palmitoyl, chloroacetyl, trichloroacetyl, trifluoroacetyl or 4-chlorobenzoyl radical.

8. The isotopic peroxide as defined in claim 5, wherein either R or R' is a hydrogen atom.

9. A process for the preparation of an $O^{17}$ isotopic peroxide compound comprising reacting $H_2O_2^{17}$ or H—$O^{17}$—$O^{16}$—H with precursor reagent thereof.

* * * * *